United States Patent
Malkowski

(10) Patent No.: US 8,876,806 B2
(45) Date of Patent: Nov. 4, 2014

(54) SURGICAL INSTRUMENT WITH ARTICULATING ASSEMBLY

(71) Applicant: Covidien LP, Mansfield, MA (US)

(72) Inventor: Jaroslaw T. Malkowski, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 145 days.

(21) Appl. No.: 13/735,062

(22) Filed: Jan. 7, 2013

(65) Prior Publication Data

US 2013/0178837 A1 Jul. 11, 2013

Related U.S. Application Data

(60) Provisional application No. 61/584,702, filed on Jan. 9, 2012.

(51) Int. Cl.
*A61B 17/00* (2006.01)
*A61B 17/02* (2006.01)
*A61B 17/29* (2006.01)

(52) U.S. Cl.
CPC ......... *A61B 17/00* (2013.01); *A61B 2017/2927* (2013.01); *A61B 17/0293* (2013.01); *A61B 17/29* (2013.01)
USPC ......... 606/1; 227/175.1; 227/175.2; 600/112; 600/141; 606/41; 606/52

(58) Field of Classification Search
CPC .......... A61B 17/14; A61B 1/04; A61B 18/18; A61B 1/00; A61B 17/10
USPC .............. 600/112, 109, 144, 141; 606/41, 52; 227/175.1, 175.2
See application file for complete search history.

(56) References Cited

U.S. PATENT DOCUMENTS

| | | | |
|---|---|---|---|
| 5,524,633 A | 6/1996 | Heaven et al. | |
| 5,762,255 A * | 6/1998 | Chrisman et al. | 227/175.2 |
| 5,989,182 A * | 11/1999 | Hori et al. | 600/112 |
| 6,858,005 B2 * | 2/2005 | Ohline et al. | 600/141 |
| 7,320,700 B2 | 1/2008 | Cooper et al. | |
| 7,510,107 B2 | 3/2009 | Timm et al. | |
| 8,292,147 B2 | 10/2012 | Viola | |
| 8,292,889 B2 | 10/2012 | Cunningham et al. | |
| 8,414,577 B2 * | 4/2013 | Boudreaux et al. | 606/41 |
| 2005/0131279 A1 * | 6/2005 | Boulais et al. | 600/141 |
| 2006/0190031 A1 | 8/2006 | Wales et al. | |
| 2007/0158385 A1 * | 7/2007 | Hueil et al. | 227/175.1 |
| 2010/0076433 A1 * | 3/2010 | Taylor et al. | 606/52 |
| 2010/0179540 A1 | 7/2010 | Marczyk et al. | |
| 2010/0249759 A1 | 9/2010 | Hinman et al. | |
| 2011/0213363 A1 | 9/2011 | Cunningham et al. | |
| 2012/0253324 A1 | 10/2012 | Lee et al. | |

* cited by examiner

*Primary Examiner* — William Thomson
*Assistant Examiner* — Victor Shapiro

(57) ABSTRACT

A surgical instrument includes a housing having an elongated member assembly extending from the housing. The elongated member has a first portion and a second portion. The second portion is movably coupled to the first portion by a cable that facilitates the relative movement of the first portion and the second portion.

20 Claims, 5 Drawing Sheets

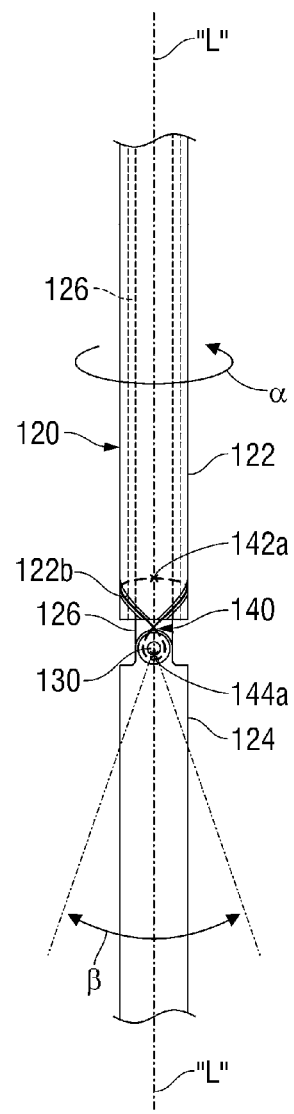
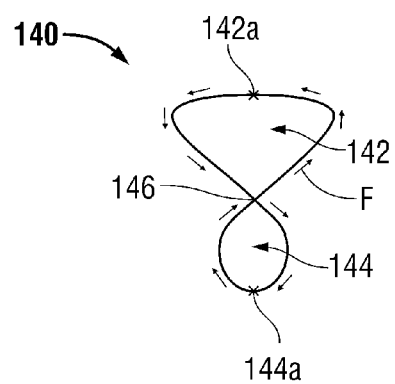
FIG. 2B
FIG. 2A
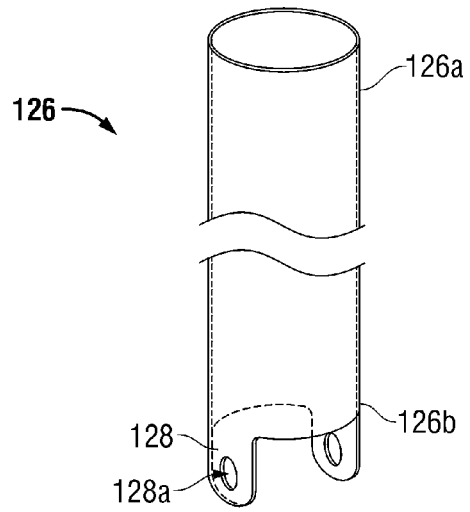
FIG. 2C

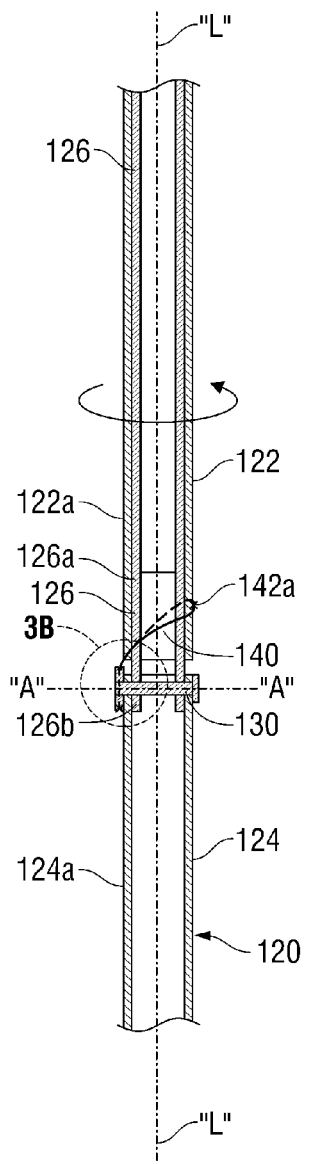
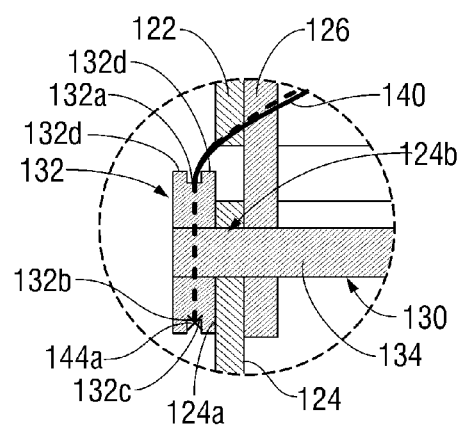
FIG. 3A
FIG. 3B

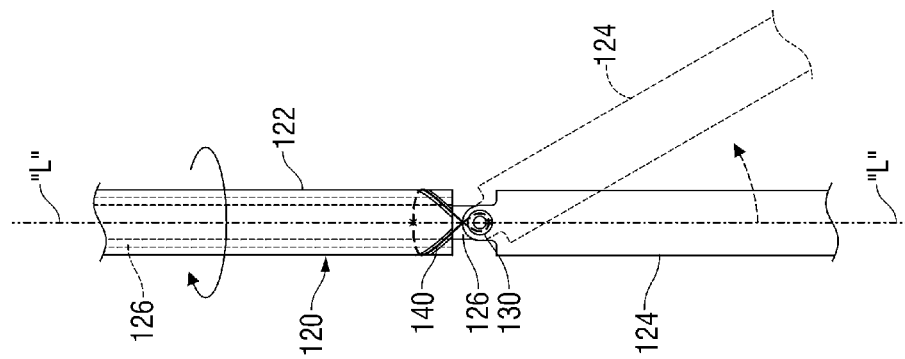
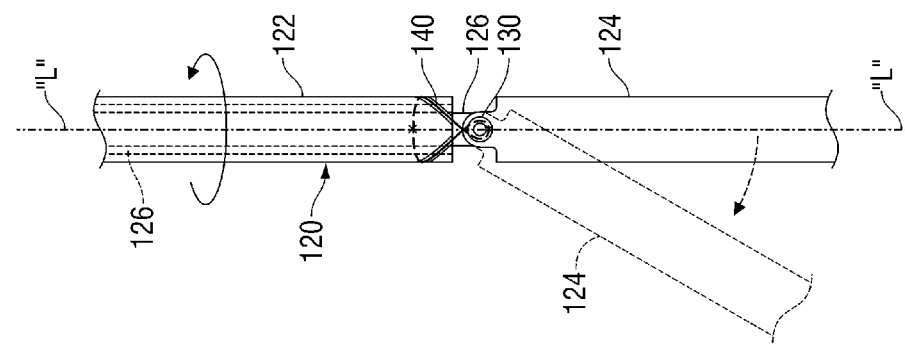

SURGICAL INSTRUMENT WITH ARTICULATING ASSEMBLY

CROSS-REFERENCE TO RELATED APPLICATIONS

This application claims the benefit of and priority to U.S. Provisional Patent Application No. 61/584,702, filed Jan. 9, 2012, the entire disclosure of which is incorporated by reference herein.

BACKGROUND

1. Technical Field

The present disclosure relates generally to surgical instruments for use during a minimally invasive surgical procedure. More particularly, the present disclosure relates to surgical instruments having articulating assemblies for use with surgical access devices.

2. Description of Related Art

Increasingly, many surgical procedures are performed through small incisions in the skin. As compared to the larger incisions typically required in traditional procedures, smaller incisions result in less trauma to the patient. By reducing the trauma to the patient, the time required for recovery is also reduced. Generally, the surgical procedures that are performed through small incisions in the skin are referred to as endoscopic. If the procedure is performed on the patient's abdomen, the procedure is referred to as laparoscopic. Throughout the present disclosure, the term minimally invasive is to be understood as encompassing both endoscopic and laparoscopic procedures.

During a typical minimally invasive procedure, surgical objects, such as surgical access devices (e.g., trocar and cannula assemblies) or endoscopes, are inserted into the patient's body through the incision in tissue. In general, prior to the introduction of the surgical object into the patient's body, insufflation gas is used to enlarge the area surrounding the target surgical site to create a larger, more accessible work area. Accordingly, the maintenance of a substantially fluid-tight seal is desirable to inhibit the escape of the insufflation gas and the deflation or collapse of an enlarged surgical site. In response to this, various access devices with sealing features are used during the course of minimally invasive procedures to provide an access for surgical objects to enter the patient's body. Some of these devices are configured for use through a single incision or a naturally occurring orifice (i.e. mouth, anus, or vagina) while allowing multiple instruments to be inserted through the device to access the working space beyond the device.

During procedures employing surgical instruments through a single incision access device, it is advantageous to move the positioning of the end effector of the surgical instrument.

One example, as disclosed by U.S. Pat. No. 5,520,678, uses control balls disposed in a proximal and distal end of a device, such that rotation and pivoting of the proximal control ball is transmitted to the distal control ball and consequently articulates an end effector at the distal end of the device.

Another example, as disclosed by U.S. Pat. No. 5,511,564, is a surgical device having a frame member with a pair of tissue holding mechanisms. An actuator mechanism allows positioning of the tissue holding mechanisms such that a portion of tissue can be stretched, providing a desirable surgical site.

However, a continuing need exists for improved articulating surgical instruments for use through single incision access devices.

SUMMARY

The present disclosure relates to a surgical instrument including a housing having an elongated member assembly extending from the housing. The elongated member assembly has a first portion and a second portion. The first portion is proximal the second portion. In addition, a support member is secured to the housing. The first portion is movably positioned about the support member to articulate the second portion relative to a longitudinal axis extending through the elongated member assembly. The first portion may define a first loop cable channel about an outer surface of the first portion.

The second portion is movably coupled to the first portion by a cable that facilitates the relative movement of the first portion and the second portion. A pivot pin is secured to the second portion and the support member. The second portion articulates about a pivot axis defined through the pivot pin relative to the first portion in response to rotation of the first portion about the longitudinal axis. The pivot axis is transverse to the longitudinal axis. The pivot pin is fixedly secured to the second portion such that force transferred through the cable upon movement of the first portion rotates the pivot pin and articulates the second portion relative to the first portion. The pivot pin may extend beyond an outer surface of the second portion to form a contacting surface. The pivot pin may define a second loop cable channel.

The cable defines a first loop and a second loop. The cable may be a single cable which crosses itself at a single point to form the first and second loops. The first loop is secured to the first portion and the second loop secured to the second portion. The first loop is fixed at a first fixed point on the first portion and the second loop is fixed at a second fixed point on the pivot pin. The first loop of the cable is at least partially disposed around an outer surface of the first portion and the second loop is at least partially disposed around an outer surface of the pivot pin. The first loop of the cable may be at least partially disposed within the first loop cable channel. The second loop of the cable may be at least partially disposed within the second loop cable channel. The second loop may be at least partially in contact with the contacting surface.

Rotational movement of the first portion tensions one or both of the first loop about the outer surface of the first portion and the second loop about the pivot pin. The tension is sufficient to articulate the second portion relative to the first portion about the pivot axis.

According to one aspect, the present disclosure relates to a surgical instrument including a cable having an intermediate section and first and second ends. The intermediate section is secured to one of the first and second portions. The first and second ends are secured to the other of the first and second portion. At least a portion of the cable defined between the ends of the cable and the intermediate section of the cable is movable relative to one or both of the first and second portions. Each of the ends of the cable and the intermediate section of the cable remains fixed to one or both of the first and second portions. The second portion articulates in relation to a longitudinal axis defined through the elongated member assembly and relative to the first portion upon rotational movement of the first portion about the longitudinal axis.

In embodiments, a coupling member is secured to the first portion. The coupling member defines a pair of lumens. Different portions of the cable extend through each respective lumen.

BRIEF DESCRIPTION OF DRAWINGS

Various embodiments of the presently disclosed device are disclosed herein with reference to the drawings, wherein:

FIG. 2A is side view of a portion of one embodiment of an elongated member assembly of the surgical instrument of FIG. 1;

FIG. 2B is a perspective view of one embodiment of a cable of the embodiment of the presently disclosed elongated member assembly shown in FIG. 1;

FIG. 2C is an enlarged perspective view of a portion of one embodiment of a support member of the embodiment of the presently disclosed elongated member assembly shown in FIG. 1;

FIG. 3A is a front, cross-sectional view of a portion of the embodiment of the presently disclosed elongated member assembly shown in FIG. 2A;

FIG. 3B is an enlarged, partial cross-sectional view of the indicated area of detail shown in FIG. 3A;

FIG. 4 is a side view of a portion of the embodiment of the presently disclosed elongated member assembly shown in FIG. 1 in a first articulated position;

FIG. 5 is a side view of a portion of the embodiment of the presently disclosed elongated member assembly shown in FIG. 1 in a second articulated position;

DETAILED DESCRIPTION OF EMBODIMENTS

Figure 1:
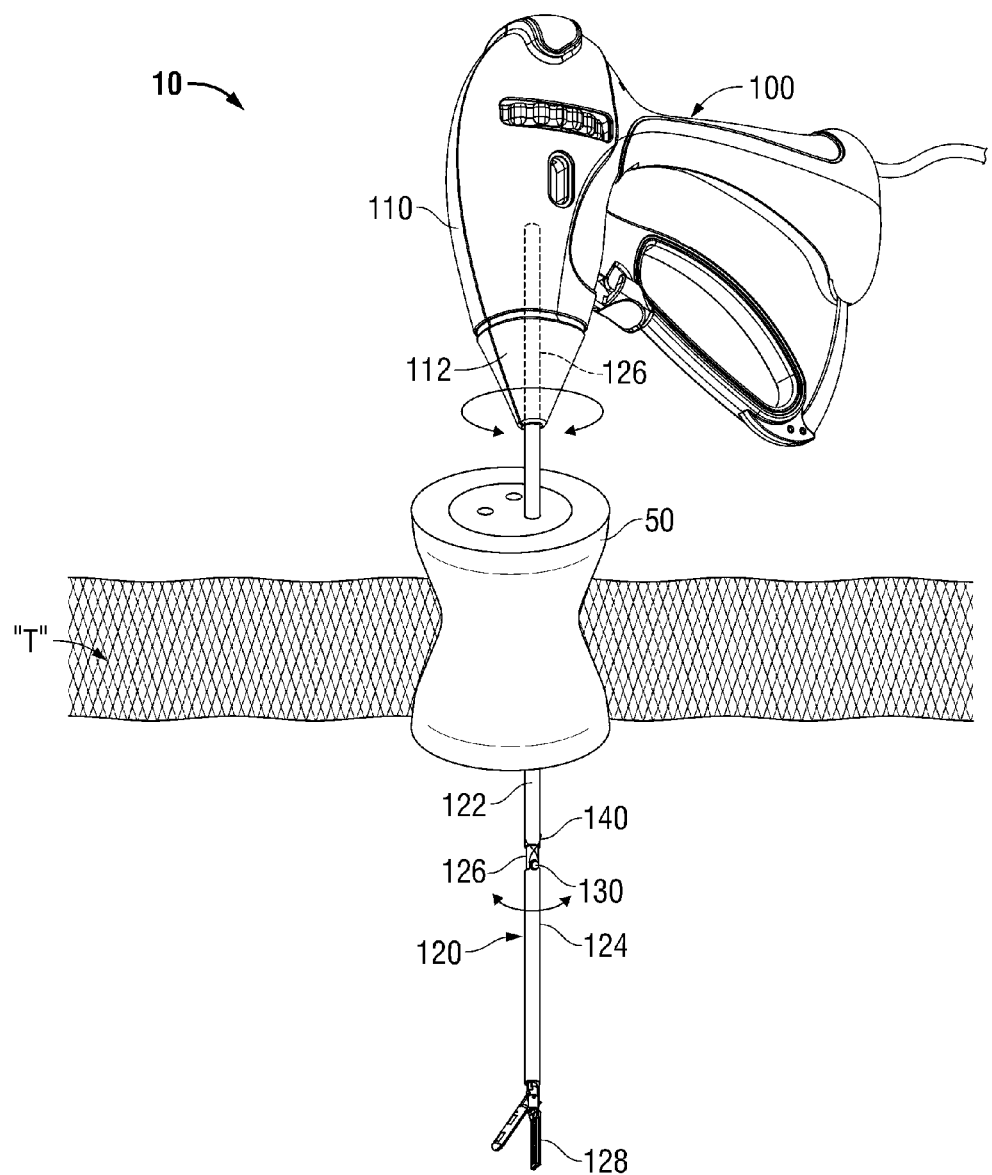
FIG. 1 is a perspective view of a surgical assembly including a surgical instrument and an access device in accordance with the present disclosure.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As shown in the drawings and as described throughout the following description, and as is traditional when referring to relative positioning on an object, the term "proximal" refers to the end of the device that is closer to the user and the term "distal" refers to the end of the device that is farther from the user. In the following description, well-known functions or constructions are not described in detail to avoid obscuring the present disclosure in unnecessary detail.

Referring initially to FIG. 1, a surgical assembly 10 includes an access device 50 and a surgical instrument 100. The access device 50 is configured for the sealed reception and passage of the surgical instrument 100 when the surgical access device 50 is positioned in tissue "T." The surgical instrument 100 includes a housing 110. The housing 110 has a knob 112 and an elongated member assembly 120 extending from the housing 110. The elongated member assembly 120 has a first portion 122, a second portion 124, and a support member 126. A pivot pin 130 mounted to the support member 126 and the second portion 124 couples the first portion 122 to the second portion 124. The first portion 122 is proximal of the second portion 124. The elongated member assembly 120 may include an end effector 128 supported on a distal end of the second portion 124.

As shown in FIGS. 2C and 3A, the support member 126 includes a proximal section 126a and a distal section 126b. Proximal section 126a of is fixedly secured to the housing 110. The support member 126 may be secured to the housing 110 by any suitable mechanical or chemical fastening means known in the art (e.g., fasteners, adhesive, hook and loop, etc.) and may be integrally formed with the housing 110. The distal portion 126b of the support member 126 is secured to the second portion 124 via the pivot pin 130. In particular, the distal portion 126b includes a pair of extensions 128 defining an aperture 128a therethrough for the reception of the pivot pin 130.

As best illustrated in FIG. 3B, the pivot pin 130 includes a wheel 132 and a pin shaft 134. The pin shaft 134 extends through both the support member 126, namely the apertures 128a of the extensions 128, and apertures 124b defined in a proximal end of the second portion 124. The pin shaft 134 is fixedly secured to the second portion 124 at opposing ends of the pin shaft 134.

With reference to FIGS. 2A and 3A, the second portion 124 is movably coupled to the first portion 122 by a cable 140 that facilitates the relative movement of the first portion 122 and the second portion 124. The second portion 124 can be articulated through angle $\beta$ (FIG. 2A) about a pivot axis "A-A" defined through the pivot pin 130. The second portion 124 articulates relative to the first portion 122 and the support member 126 in response to rotation of the first portion 122 through angle $\alpha$ (FIG. 2A). In particular, the first portion 122 rotates about a longitudinal axis "L-L" defined through the first and second portions 122, 124 and about support member 126. The pivot axis "A-A" is transverse to the longitudinal axis "L-L."

Briefly referring to FIGS. 2B, 4, and 5, the pivot pin 130 is fixedly secured to the second portion 124 such that force "F" (FIG. 2B) transferred through the cable 140 upon movement of the first portion 122 rotates the pivot pin 130 via the wheel 132 and articulates the second portion 124 relative to the first portion 122. As best shown in FIGS. 3A and 3B, the wheel 132 extends beyond an outer surface 124a of the second portion 124. The wheel 132 includes a contacting surface 132b that engages the cable 140. The contacting surface 132b extends along an outer surface 132a of the wheel 132.

As depicted in FIG. 2B, the cable 140 defines a first loop 142 and a second loop 144. The cable 140 may be a single cable or multiple cables which form a unified structure. The cable 140 crosses itself at a single point 146 to form the first and second loops 142, 144. Referring again to FIGS. 2A, 3A, and 3B, the first loop 142 is secured to the first portion 122. The second loop 144 is indirectly secured to the second portion 124 via the wheel 132 of the pivot pin 130. The first loop 142 is at least partially disposed around an outer surface 122a of the first portion 122 and the second loop 144 is at least partially disposed around the outer surface 132a of the wheel 132 of the pivot pin 130 along the contacting surface 132b. The first loop 142 is fixed, e.g., pinched, at a first fixed point 142a on the first portion 122 and the second loop 144 is fixed, e.g., pinched, at a second fixed point 144a on the wheel 132 of the pivot pin 130. The first portion 122 may define a first loop cable channel 122b about an outer surface 122a of the first portion 122. As best depicted in FIG. 2A, the first loop 142 of the cable 140 may be at least partially disposed within the first loop cable channel 122b. FIGS. 3A and 3B illustrate that the second loop 144 may be at least partially in contact with the contacting surface 132b of the wheel 132 of the pivot pin 130. With brief reference again to FIG. 3B, the wheel 132 defines a second loop cable channel 132c between a pair of annular members 132d extending from the wheel 132. The second loop 142 of the cable 140 may be at least partially disposed within the second loop cable channel 132c.

In use, and as seen in FIGS. 4 and 5, rotational movement of the first portion 122 tensions one or both of the first loop 142 and the second loop 144. The first loop 142 tensions about the outer surface 122a of the first portion 122 and the second loop 144 tensions about the wheel 132 of the pivot pin 130. The cumulative applied tension in the cable 140, including tension in the first and/or second loops 142, 144 is sufficient to articulate the second portion 124 relative to the first portion 122 about the pivot axis "A-A" (FIG. 3A) and across longitudinal axis "L-L."

Figure 6C:
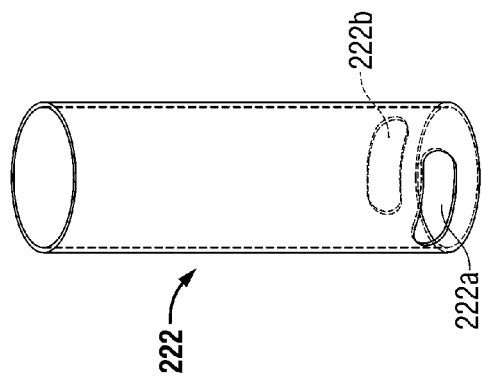
FIG. 6C is an enlarged perspective view of a portion of one embodiment of a first portion of the embodiment of the presently disclosed elongated member assembly shown in FIGS. 6A and 6B.
Figure 6B:
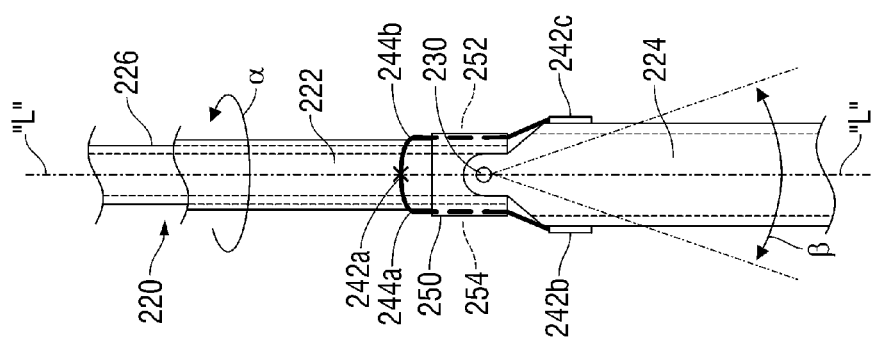
FIG. 6B is a side view of a portion of the embodiment of the presently disclosed elongated member assembly shown in FIG. 6A.
Figure 6A:
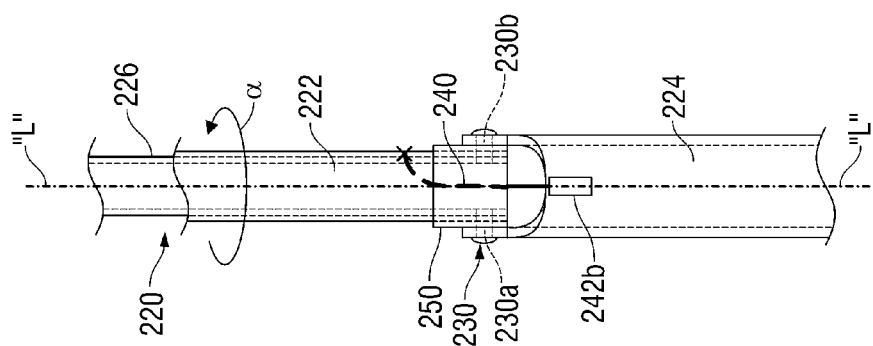
FIG. 6A is a front view of a portion of another embodiment of the presently disclosed elongated member assembly in accordance with the present disclosure.

Turning now to FIGS. 6A-6B, another embodiment of an elongated member assembly, generally referred to as 220, is similar to elongated member assembly 120 and is described herein only to the extent necessary to describe the differences in construction and operation thereof. The elongated member assembly 220 has a first portion 222, a second portion 224, a support member 226, one or more pivot pins 230, a cable 240, and a coupling member 250.

As best illustrated in FIG. 6B, the second portion 224 articulates through an angle β in relation to a longitudinal axis "L" defined through the elongated member assembly 220 upon rotational movement of the first portion 222 via knob 112 (FIG. 1) about the longitudinal axis "L" and about the support member 226. The support member 226 remains fixed to the housing 110 in a stationary position. In this regard, the second portion 224 articulates relative to the first portion 222 and the support member 226.

With reference to FIG. 6A, pivot pins 230a and 230b are secured to the first portion 222, the second portion 224, and the support member 226 to facilitate the relative movement of second portion 224 relative to the first portion 222 and the support member 226. In this regard, the pivot pins 230a, 230b pivot relative to support member 226 and first portion 222 while remaining fixed to second portion 224 to articulate second portion 224 when the pivot pins 230a, 230b are pivoting. To pivot the pivot pins 230a, 230b, the second portion 224 is movably coupled to the first portion 222 by the cable 240. The cable 240 facilitates the relative movement of the first portion 222 and the second portion 224. More specifically, first portion 222 is secured to cable 240 (described in greater detail below) and is rotatable about support member 226 to apply force to cable 240.

With brief reference to FIG. 6C, to rotate first portion 222 about pivot pins 230a, 230b, first portion 222 defines a pair of elongate channels 222a, 222b. The elongate channels 222a, 222b accommodate the pivot pins 230a, 230b in a manner sufficient to enable the pivot pins 230a, 230b to pivot while the enabling the first portion 222 to rotate about the longitudinal axis "L." Upon rotation of the first portion 222, the force applied to the cable 240 enables the second portion 224 to articulate while the pivot pins 230a, 230b pivot.

The cable 240 includes an intermediate section 242a and first and second ends 242b, 242c. The intermediate section 242a may be secured to either one of the first and second portions 222, 224. The first and second ends 242b, 242c may be secured to the other of the first and second portion 222, 224. For illustrative purposes, FIGS. 6A and 6B show the intermediate section 242a fixed to the first portion 222 and the first and second ends 242b, 242c fixed on opposed sides of the second portion 224. However, as can be appreciated, the intermediate section 242a can be fixed to the second portion 224 and the first and second ends 242b, 242c can be fixed on opposed sides of the first portion 222. At least a portion of the cable 240 defined between one or both of the first and second ends 242b, 242c of the cable 240 and the intermediate section 242a of the cable 240 is movable (e.g., portions 244a, 244b) relative to one or both of the first and second portions 222, 224. At the same time, each of the ends 242b, 242c of the cable 240 and the intermediate section 242a of the cable 240 remains fixed to one or both of the first and second portions 222, 224.

With continued reference to FIG. 6B, the coupling member 250 is secured to the first portion 222 and may be integrally formed with the first portion 222. The coupling member 250 defines a pair of lumens 252, 254. Different portions of the cable 240 extend through each respective lumen 252, 254. In embodiments, the coupling member 250 may include elongate channels similar or identical to elongated channels 222a, 222b to accommodate the pivot pins 230a, 230b in a manner sufficient to enable the pivot pins 230a, 230b to pivot while the enabling the coupling member 250 to rotate about the longitudinal axis "L" with the first portion 222.

It will be understood that various modifications may be made to the embodiments of the presently disclosed device. Therefore, the above description should not be construed as limiting, but merely as exemplifications of embodiments. Those skilled in the art will envision other modifications within the scope and spirit of the present disclosure.

What is claimed is:

1. A surgical instrument, comprising:
    a housing including an elongated member assembly extending from the housing, the elongated member assembly having a first portion and a second portion, the second portion being movably coupled to the first portion by a cable that facilitates the relative movement of the first portion and the second portion, the cable defining a first loop and a second loop, the first loop secured to the first portion, the second loop secured to the second portion, the first portion defining a first loop cable channel about an outer surface of the first portion, the first loop of the cable being at least partially disposed within the first loop cable channel.

2. The surgical instrument according to claim 1, wherein the first portion is proximal of the second portion.

3. The surgical instrument according to claim 1, further including a support member secured to the housing, the first portion movably positioned about the support member to articulate the second portion relative to a longitudinal axis extending through the elongated member assembly.

4. The surgical instrument according to claim 3, further including a pivot pin secured to the second portion and the support member.

5. The surgical instrument according to claim 4, wherein the second portion articulates about a pivot axis defined through the pivot pin relative to the first portion in response to rotation of the first portion about the longitudinal axis.

6. The surgical instrument according to claim 5, wherein the pivot axis is transverse to the longitudinal axis.

7. The surgical instrument according to claim 4, wherein the first loop is at least partially disposed around an outer surface of the first portion and the second loop is at least partially disposed around an outer surface of the pivot pin.

8. The surgical instrument according to claim 7, wherein rotational movement of the first portion tensions at least one of the first loop about the outer surface of the first portion and the second loop about the pivot pin, the tension being sufficient to articulate the second portion relative to the first portion about the pivot axis.

9. The surgical instrument according to claim 4, wherein the pivot pin is fixedly secured to the second portion such that force transferred through the cable upon movement of the first portion rotates the pivot pin and articulates the second portion relative to the first portion.

10. The surgical instrument according to claim 4, wherein the pivot pin defines a second loop cable channel, the second loop of the cable being at least partially disposed within the second loop cable channel.

11. The surgical instrument according to claim 4, wherein the pivot pin extends beyond an outer surface of the second portion to form a contacting surface, the second loop being at least partially in contact with the contacting surface.

12. The surgical instrument according to claim 4, wherein the first loop is fixed at a first fixed point on the first portion and the second loop is fixed at a second fixed point on the pivot pin.

13. A surgical instrument, comprising:
a housing including an elongated member assembly extending from the housing, the elongated member assembly having a first portion and a second portion, the second portion being movably coupled to the first portion by a cable that facilitates the relative movement of the first portion and the second portion, the cable defining a first loop and a second loop, the first loop secured to the first portion, the second loop secured to the second portion, the cable being a single cable which crosses itself at a single point to form the first and second loops.

14. A surgical instrument, comprising:
a housing including an elongated member assembly extending from the housing, the elongated member assembly having a first portion and a second portion, the second portion being movably coupled to the first portion by a cable that facilitates the relative movement of the first portion and the second portion, the cable including an intermediate section and first and second ends, the intermediate section being secured to one of the first and second portions, the first and second ends being secured to the other of the first and second portion, the second portion being articulable in relation to a longitudinal axis defined through the elongated member assembly and relative to the first portion upon rotational movement of the first portion about the longitudinal axis.

15. The surgical instrument according to claim 14, wherein at least a portion of the cable defined between at least one of the ends of the cable and the intermediate section of the cable is movable relative to at least one of the first and second portions and each of the ends of the cable and the intermediate section of the cable remains fixed to at least one of the first and second portions.

16. The surgical instrument according to claim 14, further including a coupling member secured to the first portion.

17. The surgical instrument according to claim 16, wherein the coupling member defines a pair of lumens, different portions of the cable extending through each respective lumen.

18. The surgical instrument according to claim 13, wherein the first portion is proximal the second portion.

19. The surgical instrument according to claim 13, further including a support member secured to the housing, the first portion movably positioned about the support member to articulate the second portion relative to a longitudinal axis extending through the elongated member assembly.

20. The surgical instrument according to claim 19, further including a pivot pin secured to the second portion and the support member.

* * * * *